(12) United States Patent
Abdur-Rashid

(10) Patent No.: US 7,816,533 B2
(45) Date of Patent: Oct. 19, 2010

(54) ASYMMETRIC IMINE HYDROGENATION PROCESSES

(76) Inventor: Kamaluddin Abdur-Rashid, 3816 Morning Star Drive, Mississauga, Ontario (CA) L4T 1Y9

( * ) Notice: Subject to any disclaimer, the term of this patent is extended or adjusted under 35 U.S.C. 154(b) by 0 days.

(21) Appl. No.: 10/596,489

(22) PCT Filed: Dec. 15, 2004

(86) PCT No.: PCT/CA2004/002130

§ 371 (c)(1), (2), (4) Date: Mar. 20, 2007

(87) PCT Pub. No.: WO2005/056513

PCT Pub. Date: Jun. 23, 2005

(65) Prior Publication Data

US 2007/0293681 A1   Dec. 20, 2007

Related U.S. Application Data

(60) Provisional application No. 60/529,084, filed on Dec. 15, 2003.

(51) Int. Cl.
*C07D 211/08* (2006.01)
(52) U.S. Cl. .................. 546/192; 548/577; 564/375
(58) Field of Classification Search .................. 564/415, 564/489, 375, 413, 448; 546/192; 548/577
See application file for complete search history.

(56) References Cited

U.S. PATENT DOCUMENTS

| | | | | |
|---|---|---|---|---|
| 6,528,687 B2 * | 3/2003 | Cobley et al. | ............... | 564/415 |
| 6,528,689 B2 * | 3/2003 | Chaudhari et al. | ........... | 568/861 |
| 7,256,311 B2 * | 8/2007 | Abdur-Rashid et al. | ..... | 564/415 |

FOREIGN PATENT DOCUMENTS

| WO | WO02/08169 | 1/2002 |
|---|---|---|
| WO | WO03/097571 | 11/2003 |
| WO | WO 03/097571 | * 11/2003 |

OTHER PUBLICATIONS

Tararov et al., Phosphines versus phosphinites as ligands in the rhodium catalyzed asymmetric hydrogenation of imines a systematic study, Tetrahedron: Asymmetry (1999), 10(20), 4009-4015.*
Abdur-Rashid, K., "RuHC (diphosphine)(diamine): Catalyst precursors for the stereoselective hydrogentation of ketones and imines", Organometallics, 2001, vol. 20, pp. 1047-1049.
Christopher J. Cobley and Julian P. Henschke. Adv.Synth. Catal. 2003. 345:195-201.

* cited by examiner

*Primary Examiner*—Jafar Parsa
*Assistant Examiner*—Chukwuma O Nwaonicha
(74) *Attorney, Agent, or Firm*—Bereskin & Parr LLP/S.E.N.C.R.L., s.r.l.; Michael Fenwick

(57) ABSTRACT

A process for the catalytic hydrogenation or asymmetric hydrogenation of imines of Formula (I) to the corresponding amines of Formula (II) is provided in which $R^1$ is aryl; $R^2$ is aryl, cyclic, alkyl, alkenyl or alkynyl; and $R^3$ is alkyl. The catalytic system includes a ruthenium complex containing (1) a diamine and (2) a diphosphine or two monodentate phosphines ligands. Such process also relates to the asymmetric hydrogenation of prochiral imines to the chiral amines using chiral ruthenium complexes bearing chiral diphosphines or chiral monodentate phosphines and chiral diamines.

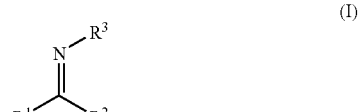

(I)

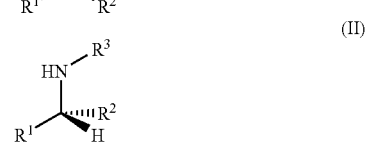

(II)

37 Claims, No Drawings

ABSTRACT IMINE HYDROGENATION PROCESSES

This application is a national phase entry of PCT/CA2004/002130, filed Dec. 15, 2004 which claims priority from U.S. Provisional patent application Ser. No. 60/529,084, filed Dec. 15, 2003.

FIELD OF THE INVENTION

The present invention relates to the field of catalytic hydrogenations, particularly catalytic asymmetric hydrogenation processes of the reduction of imines to amines in which the catalytic system includes a ruthenium complex containing (1) a diamine and (2) a diphosphine or two monodentate phosphines ligands.

BACKGROUND OF THE INVENTION

There is continuously a growing demand for enantiomerically pure amines in the pharmaceutical, agrochemical and fine chemicals industries. Over the past decade, there has been significant efforts directed towards developing procedures for asymmetric imine hydrogenations. Although many highly enantioselective chiral catalysts and catalytic processes are available for the asymmetric hydrogenation and transfer hydrogenation of C=C and C=O bonds, there are only a few widely applicable and feasible processes for effective reduction of the analogous C=N function of imines. The production of chiral amines via this methodology still represents a major challenge.

In 1997, B. R. James reviewed the preparation of chiral amines by homogeneous catalytic hydrogenation reactions involving metal complexes (James, *Catalysis Today* 1997, 37, 209-221). The review by James names several systems based on rhodium for the asymmetric hydrogenation of imines but they suffer from drawbacks, such as low enantioselectivity or severe reaction conditions. In U.S. Pat. No. 6,037,500, X. Zhang et al. disclosed the use of BICP, a chiral diphosphine ligand, on rhodium and iridium in the asymmetric hydrogenation of internal C=N bonds at 1000 psi $H_2$ at room temperature to produce amines with e.e. ranging from 65 to 94%. Spindler and co-workers demonstrated the use of in situ generated iridium JOSIPHOS complexes for the enantioselective hydrogenation of imines (Spindler et al., *Angew. Chem., Int. Ed. Engl.*, 1990, 29, 558; Blaser and Spindler, *Topics in Catalysis*, 1997, 4, 275). This process was subsequently modified and applied to the industrial production of the imine precursor to (S)-Metolachlor, a valuable agrochemical product, then for Ciba-Giegy, now for Novartis. The production of S-Metolachlor is an example of a large-scale industrial process that depends on the homogenous hydrogenation of a prochiral imine.

Buchwald and co-workers prepared and effectively employed various chiral ansa-titanocene complexes for both hydrogenation and hydrosilylation of imines (Willoughby and Buchwald, *J. Am. Chem. Soc.*, 1992, 114, 7562; *J. Am. Chem. Soc.*, 1994, 116, 8952 and 11703). The need to activate the catalyst by the addition of butyl-lithium and phenyl silane limits the scope and applicability of this process. This system also suffers from the drawback of being very oxygen and water sensitive.

A recent article by Tang and Zhang provides a comprehensive review on other advances in enantioselective hydrogenation of imines (Tang and Zhang, *Chem. Rev.* 2003, 103, 3029). These include several recent examples of the development and use of chiral complexes of rhodium (Buriak et al., *Organometallics* 1996, 15, 3161; Spindler et al., *Adv. Synth. Catal.* 2001, 343, 68), iridium (Bianchini et al., *Organometallics* 1998, 17, 3308; Kainz et al., *J. Am. Chem. Soc.*, 1999, 121, 6421; Zhang et al., *Angew. Chem. Int. Ed. Engl.* 2001, 40, 3425) and palladium (Abe et al., *Org. Lett.* 2001, 3, 313) and their use for the asymmetric hydrogenation of various cyclic and acyclic imines.

Despite the reported successes of some of these catalytic hydrogenation processes for imines, there are certain significant drawbacks. These include high operating pressures (typically >50 bar $H_2$), high catalyst loading and the use of expensive iridium- and rhodium-based systems. In addition, activity and/or enantioselectivity tends to be either low or highly substrate dependent, which in some cases necessitates the development of an entire catalytic system and process for only one substrate or a very closely related group of substrates.

Recently Rautenstrauch et al. reported the use of metal complexes with P—N bidentate ligands (WO 02/22526 A2) and PNNP tetradentate ligands (WO 02/40155 A1) in the catalytic hydrogenation of C=O and C=N carbon-heteroatom double bonds for the production of alcohols and amines, respectively. Noyori and coworkers have also described an efficient catalyst system generated from the complex $Ru(\eta^6$-arene)(tosyldiamine)Cl for the asymmetric hydrogenation of imines by transferring hydrogen from triethylammonium formate (Noyori et al., *Acc. Chem. Res.* 1997, 30, 97-102).

Noyori and co-workers have pioneered the use of ruthenium complexes bearing a chelating diphosphine ligand (or two monodentate phosphines) and a chelating diamine ligand for the catalytic asymmetric hydrogenation of ketones. At least one and usually both of the chelating ligands are chiral. The various papers and patents of Noyori et al. have demonstrated the highly efficient reduction of various functionalised and unfunctionalised ketones using this class of catalysts. It was also demonstrated by Noyori and co-workers (Ohkuma et al., *J. Am. Chem. Soc.*, 1995, 107, 2675 and 10417) that a fully isolated and characterised ruthenium(II)diphosphinediamine complex could be used as catalyst. High activity and high selectivity were generally associated with the use of chiral biaryl-phosphines (eg. Tol-BINAP and Xyl-BINAP) and diamines (eg. DPEN and DAIPEN) as ligands.

It has been reported that similar classes of Noyori-type ruthenium(II)(phosphine)$_2$(diamine) complexes could catalyse the hydrogenation and asymmetric hydrogenation of activated (aromatic) imines (Abdur-Rashid et al., *Organometallics*, 2000, 20, 1655) or ruthenium(II)diphosphinediamine complexes (Abdur-Rashid et al., Presentations at The Canadian Society for Chemistry 83$^{rd}$ Conference and Exhibition, Calgary, Alberta, May 2000, and subsequently Abdur-Rashid et al., *Organometallics*, 2001, 21, 1047). Since these publications, Chirotech Technology Limited has also reported similar imine hydrogenation processes (Cobley et al. WO 02/08169 A1; Cobley at al. *Adv. Synth. Catal.* 2003, 345, 195) based on similar classes of complexes and imine substrates. It is noted that the reports of Abdur-Rashid et al. and Chirotech Technology Limited both relate to the use of Noyori-type ruthenium(II)-(phosphine)$_2$(diamine) and ruthenium(II) diphosphinediamine complexes as catalysts for the reduction of activated imines of the Formula A shown below in which R represents an activating aryl group, R' represents an alkyl group and R" represents either an aryl or benzyl group.

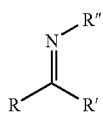

A

In yet another publication (Abdur-Rashid et al., PCT/CA03/00689), the use of other similar Noyori-type ruthenium(II) complexes for the hydrogenation and asymmetric hydrogenation of unactivated imines has been reported, in which R and R' in the Formula A simultaneously or independently represent alkyl or alkenyl substituents and R" represents either an aryl, alkyl or alkenyl substituent. The imines described in this latter publication are inherently more difficult to reduce than the activated (aromatic) analogues reported by Chirotech.

To date, there are no reports in the literature which teach the use of such Noyori-type catalysts in hydrogenation processes for the reduction of a class of imines in which, in Formula A, R represents aryl; R' represents cyclic, alkyl, alkenyl, alkynyl or aryl; and R" represents cyclic or acyclic alkyl.

There is also a continuing demand for an enantioselective imine hydrogenation procedure that allows for the facile preparation of chiral primary amines in high yields and stereoselectivities. Such chiral primary amines are desired as valuable precursors, intermediates and end products in the pharmaceutical, agrochemical, fine chemical and material industries.

SUMMARY OF THE INVENTION

It has now been found that hydrogenation of the carbon-nitrogen double bond (C=N) of imines of Formula (I) to the corresponding amines of Formula (II) can be efficiently carried out using a catalytic system including a ruthenium complex containing (1) a diamine and (2) a diphosphine or two monodentate phosphine ligands.

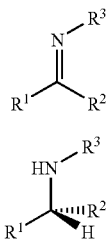

Therefore, the present invention includes a process for the hydrogenation of the carbon-nitrogen double bond (C=N) of imines of Formula (I) to the corresponding amines of Formula (II) comprising contacting the imines of Formula (I) with molecular hydrogen ($H_2$) and a catalytic system including a ruthenium complex containing (1) a diamine and (2) a diphosphine or two monodentate phosphine ligands. Such processes also relate to the asymmetric hydrogenation of prochiral imines to the chiral amines using chiral ruthenium complexes bearing chiral diphosphines or chiral monodentate phosphines and chiral diamines.

Accordingly, the present invention relates to a process for the hydrogenation and/or asymmetric hydrogenation of an imine of Formula (I) to an amine of Formula (II):

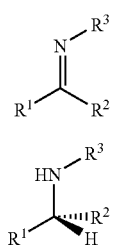

wherein $R^1$ is selected from the group consisting of aryl and heteroaryl, which two groups are optionally substituted;

$R^2$ is selected from the group consisting of hydrogen, aryl, heteroaryl, $C_{1-10}$alkyl $C_{2-10}$alkenyl, $C_{2-10}$alkynyl, $C_{3-10}$cycloalkyl, $C_{3-10}$cycloalkenyl and $C_{3-10}$heterocyclo, which latter eight groups are optionally substituted; and $R^3$ is selected from the group consisting of optionally substituted $C_1$ to $C_2$ alkyl and optionally substituted $C_{3-10}$cycloalkyl;

or $R^1$ and $R^2$ or $R^2$ and $R^3$ are linked to form an optionally substituted ring;

wherein the optional substituents of $R^1$ and $R^2$ are independently selected from one or more of the group consisting of halo, $NO_2$, $OR^4$, $NR^4{}_2$ and $R^4$, in which $R^4$ is independently selected from one or more of the group consisting of hydrogen, aryl, $C_{1-6}$alkyl $C_{2-6}$alkenyl, $C_{1-6}$cycloalkyl and $C_{1-6}$cycloalkenyl;

the optional substituents of $R^3$ are independently selected from one or more of the group consisting of halo, $NO_2$, $OR^5$, $NR^5{}_2$ and $R^5$, in which $R^5$ is independently selected from the group consisting of $C_{1-6}$alkyl, $C_{2-6}$alkenyl and $C_{2-6}$alkynyl; and one or more of the carbon atoms in the alkyl alkenyl and/or alkynyl groups of $R^1$, $R^2$ and/or $R^3$ is optionally replaced with a heteroatom selected from the group consisting of O, S, N, P and Si, which, where possible, is optionally substituted with one or more $C_{1-6}$alkyl groups, said process comprising the steps of reacting imines of Formula (I) in the presence of $H_2$, a base and a catalytic system in which the catalytic system includes a base and a ruthenium complex comprising (1) a diamine and (2) a diphosphine ligand or monodentate phosphine ligands.

In an embodiment, the present invention also relates to a process for the hydrogenation and/or asymmetric hydrogenation of an imine of Formula (III) to an amine of Formula (IV):

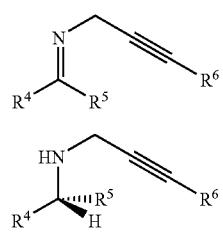

wherein $R^4$ and $R^5$ represent simultaneously or independently any substituent, including but not limited to hydrogen, aryl, heteroaryl, $C_{1-10}$alkyl $C_{2-10}$alkenyl, $C_{2-10}$alkynyl, $C_{3-10}$cycloalkyl, $C_{3-10}$cycloalkenyl and $C_{3-10}$heterocyclo, which latter eight groups are optionally substituted, or $R^4$ and $R^5$ are linked together to form an optionally substituted ring;

$R^6$ is selected from the group consisting of H, aryl, $C_{1-10}$alkyl $C_{2-10}$alkenyl, $C_{2-10}$alkynyl, $C_{3-10}$cycloalkyl and $C_{3-10}$cycloalkenyl, which latter six groups are optionally substituted;

wherein the optional substituents of $R^4$, $R^5$ and $R^6$ are independently selected from one or more of the group consisting of halo, $NO_2$, $OR^7$, $NR^7_2$ and $R^7$, in which $R^7$ is independently selected from the group consisting of $C_{1-6}$alkyl, $C_{2-6}$alkenyl and $C_{2-6}$alkynyl; and one or more of the carbon atoms in the alkyl, alkenyl and/or alkynyl groups of $R^4$, $R^5$ and/or $R^6$ are optionally replaced with a heteroatom selected from the group consisting of O, S, N, P and Si, which, where possible, is optionally substituted with one or more $C_{1-6}$alkyl groups, said process comprising the steps of reacting imines of Formula (III) in the presence of $H_2$, a base and a catalytic system in which the catalytic system includes a base and a ruthenium complex comprising (1) a diamine and (2) a diphosphine ligand or monodentate phosphine ligands.

The present invention also relates to a very effective process for the preparation of primary amines of Formula V, by selectively removing the propargyl group from the secondary amine of the Formula IV.

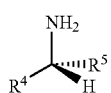

The processes of the invention may, in particular be applied to the preparation of enantiomerically enriched chiral amines of Formulae (II), (IV) and (V), or the opposite enantiomers thereof.

In embodiments of the invention, the ruthenium complex has the general Formula $RuXY(PR_3)_2(NH_2—Z—NH_2)$ (VI) or $RuXY(R_2P-Q-PR_2)(NH_2—Z—NH_2)$ (VII), where Z and Q represent a chiral or achiral linker; the ancilliary ligands $PR_3$ and $R_2P-Q-PR_2$ represent monodentate and bidentate phosphines, respectively; and the ligands X and Y represent an anionic ligand.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

In one of its embodiments, the present invention relates to a process for the hydrogenation and/or asymmetric hydrogenation of an imine of Formula (I) to an amine of Formula (II) and/or its other enantiomer:

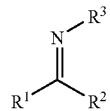

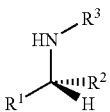

wherein $R^1$ is selected from the group consisting of aryl and heteroaryl which two groups are optionally substituted;

$R^2$ is selected from the group consisting of hydrogen, aryl, heteroaryl, $C_{1-10}$alkyl $C_{2-10}$alkenyl, $C_{2-10}$alkynyl, $C_{3-10}$cycloalkyl, $C_{3-10}$cycloalkenyl and $C_{3-10}$heterocyclo, which latter eight groups are optionally substituted; and $R^3$ is selected from the group consisting of optionally substituted $C_1$ to $C_2$ alkyl and optionally substituted $C_{3-10}$cycloalkyl;

or $R^1$ and $R^2$ or $R^2$ and $R^3$ are linked to form an optionally substituted ring;

wherein the optional substituents of $R^1$ and $R^2$ are independently selected from one or more of the group consisting of halo, $NO_2$, $OR^4$, $NR^4_2$ and $R^4$, in which $R^4$ is independently selected from one or more of the group consisting of hydrogen, aryl, $C_{1-6}$alkyl $C_{2-6}$alkenyl, $C_{3-6}$cycloalkyl and $C_{3-6}$cycloalkenyl;

the optional substituents of $R^3$ are independently selected from one or more of the group consisting of halo, $NO_2$, $OR^5$, $NR^5_2$ and $R^5$, in which $R^5$ is independently selected from the group consisting of $C_{1-6}$alkyl, $C_{2-6}$alkenyl and $C_{2-6}$alkynyl; and one or more of the carbon atoms in the alkyl alkenyl and/or alkynyl groups of $R^1$, $R^2$ and/or $R^3$ is optionally replaced with a heteroatom selected from the group consisting of O, S, N, P and Si, which, where possible, is optionally substituted with one or more $C_{1-6}$alkyl groups, said process comprising the steps of reacting imines of Formula (I) in the presence of $H_2$, and a catalytic system in which the catalytic system includes a base and a ruthenium complex comprising (1) a diamine and (2) a diphosphine ligand or monodentate phosphine ligands.

In another embodiment, the present invention also relates to a process for the hydrogenation and/or asymmetric hydrogenation of an imine of Formula (III) to an amine of Formula (IV):

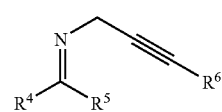

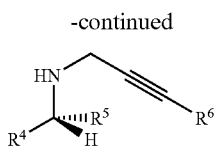

wherein $R^4$ and $R^5$ represent simultaneously or independently any substituent, including but not limited to hydrogen, aryl, heteroaryl, $C_{1-10}$alkyl $C_{2-10}$alkenyl, $C_{2-10}$alkynyl, $C_{3-10}$cycloalkyl, $C_{3-10}$cycloalkenyl and $C_{3-10}$heterocyclo, which latter eight groups are optionally substituted, or $R^4$ and $R^5$ are linked together to form an optionally substituted ring;

$R^6$ is selected from the group consisting of H, aryl, $C_{1-10}$alkyl $C_{2-10}$alkenyl, $C_{2-10}$alkynyl, $C_{3-10}$cycloalkyl and $C_{3-10}$cycloalkenyl, which latter six groups are optionally substituted;

wherein the optional substituents of $R^4$, $R^5$ and $R^6$ are independently selected from one or more of the group consisting of halo, $NO_2$, $OR^7$, $NR^7_2$ and $R^7$, in which $R^7$ is independently selected from the group consisting of $C_{1-6}$alkyl, $C_{2-6}$alkenyl and $C_{2-6}$alkynyl; and one or more of the carbon atoms in the alkyl, alkenyl and/or alkynyl groups of $R^4$, $R^5$ and/or $R^6$ are optionally replaced with a heteroatom selected from the group consisting of O, S, N, P and Si, which, where possible, is optionally substituted with one or more $C_{1-6}$alkyl groups, said process comprising the steps of reacting imines of Formula (III) in the presence of $H_2$, and a catalytic system in which the catalytic system includes a base and a ruthenium complex comprising (1) a diamine and (2) a diphosphine ligand or monodentate phosphine ligands.

The present invention also relates to a very effective process for the preparation of primary amines of Formula V, by selectively removing the propargyl group from the secondary amine of the Formula IV.

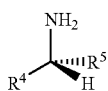

The processes of the invention may, in particular be applied to the preparation of enantiomerically enriched chiral amines of Formulae (II), (IV) and (V), or the opposite enantiomers thereof. Suitably, the processes of the present invention provide an effective means of preparing a wide range of chiral amines. It is desirable that the enantiomeric enrichment of the amines (II) and (IV) is at least 50% ee, and more suitably at least 80% ee, or higher. If necessary, any shortfall in ee can be subsequently corrected by crystallization techniques known by persons skilled in the art. It is also desirable to achieve a high conversion of substrate to product, suitably at least 80% conversion, and more suitably at least 90% conversion.

The term "aryl" as used herein means an unsaturated aromatic carbocyclic group containing from six to fourteen carbon atoms having a single ring (e.g., phenyl) or multiple condensed (fused) rings (e.g., naphthyl or anthryl). In an embodiment of the invention, aryl includes phenyl and naphthyl, in particular phenyl.

The term "heteroaryl" as used herein means an unsaturated aromatic carbocyclic group containing from five to fourteen carbon atoms having a single ring or multiple condensed (fused) and wherein one or more, suitably one or three, more suitably one to two, even more suitably one of the carbon atoms in the aromatic group is replaced with a heteroatom selected from the group consisting of O, S, and N which, where possible, is optionally substituted with one or more alkyl groups. Examples of suitable heteroaryl groups include, but are not limited to, pyridyl, thienyl, furanyl, pyrrolyl, and their corresponding benzo-fused ring systems (for example indolyl and benzofuranyl) and the like.

The term "alkyl" as used herein means a saturated, linear or branched alkyl group containing the specified number of carbon atoms.

The term "cycloalkyl" as used herein means a saturated carbocyclic group containing the specified number of carbon atoms and having a single ring (e.g., cyclohexyl and cyclopentyl) or multiple condensed (fused) rings (e.g decahydronaphthalene and adamantanyl).

The term "alkenyl" as used herein means an unsaturated, linear or branched alkenyl group containing the specified number of carbon atoms and includes vinyl, allyl, butenyl and the like. The alkenyl groups may contain any number of double bonds. Suitably, the alkenyl group contains one double bond.

The term "cycloalkenyl" as used herein means a unsaturated carbocyclic group containing the specified number of carbon atoms and having a single ring (e.g., cyclohexenyl and cyclopentenyl) or multiple condensed (fused) rings (e.g octahydronaphthalene). The cycloalkenyl groups may contain any number of double bonds. Suitably, the cycloalkenyl group contains one double bond The term "alkynyl" as used herein means an unsaturated, linear or branched alkynyl group containing the specified number of carbon atoms and includes ethynyl, propynyl, propargyl, butynyl and the like. The alkynyl groups may contain any number of triple bonds. Suitably, the alkynyl group contains one triple bond.

The term "halo" as used herein means halogen and includes chloro, bromo, iodo, fluoro and the like.

When $R^1$ and $R^2$ are linked together, or with $R^3$, or when $R^5$ and $R^6$ are linked together to form one or more carbocyclic rings, said rings may contain from three to twelve atoms, suitably three to ten atoms, having a single ring structure or multiple condensed (fused) ring structure. Further in the rings, one or more, suitably one or two, more suitably one, of the carbon atoms may be substituted with a heteroatom selected from O, S, N, P and Si, which where possible, is optionally substituted with one or more $C_{1-6}$alkyl groups. Suitably, one or more, more suitably one or two, even more suitably one, of the carbon atoms of the ring may be substituted with a heteroatom selected from O, S, N, NH and N—$CH_3$.

In the compounds of Formula I, $R^1$ is selected from the group consisting of aryl and heteroaryl, which two groups are optionally substituted. In embodiments of the invention $R^1$ is optionally substituted aryl, suitably optionally substituted phenyl, more suitably unsubstituted phenyl.

Further, in the compounds of Formula I, $R^2$ is selected from the group consisting of hydrogen, aryl, heteroaryl, $C_{1-10}$alkyl, $C_{2-10}$alkenyl, $C_{2-10}$alkynyl, $C_{3-10}$cycloakyl, $C_{3-10}$cycloalkenyl and $C_{3-10}$heterocyclo, which latter eight groups are optionally substituted. In embodiments of the invention $R^2$ is selected from the group consisting of hydrogen, aryl, $C_{1-6}$alkyl, $C_{2-6}$alkenyl, $C_{2-6}$alkynyl, $C_{3-6}$cycloalkyl and $C_{3-6}$cycloalkenyl, which latter six groups are optionally substituted. In further embodiments of the invention, $R^2$ is selected from the group consisting of hydrogen, aryl and $C_{1-6}$alkyl, which latter two groups are optionally substituted. In still further embodiments of the invention $R^2$ is selected from the group consisting of hydrogen, phenyl, and $C_{1-6}$alkyl, which latter two groups are optionally substituted. In still further embodiments of the invention $R^2$ is selected from the group consisting of hydrogen, unsubstituted phenyl and methyl.

Still further, in the compounds of Formula I, $R^3$ is selected from the group consisting of optionally substituted $C_1$ to $C_2$ alkyl and optionally substituted $C_{3-10}$cycloalkyl. In embodiments of the invention, $R^3$ is selected from the group consisting of optionally substituted $C_1$ to $C_2$ alkyl and optionally substituted $C_{3-6}$cycloalkyl. In a further embodiment of the invention, $R^3$ is methyl, ethyl i-propyl (ethyl substituted with methyl), cyclopropyl, cyclobutyl, cyclopentyl or cyclohexyl, which latter four groups are unsubstituted.

The invention also extends to compounds of Formula I wherein $R^1$ and $R^2$ or $R^2$ and $R^3$ are linked to form an optionally substituted ring. In embodiments of the invention $R^2$ and $R^3$ (including the atoms to which they are attached) are linked to form an optionally substituted, suitably unsubstituted, 5- or 6-membered ring, with the linking group being a $C_3$ to $C_4$ alkylene group.

As stated above, the optional substituents for $R^1$ and $R^2$ in the compounds of Formula I, are independently selected from one or more of the group consisting of halo, $NO_2$, $OR^4$, $NR^4_2$ and $R^4$, in which $R^4$ is independently selected from one or more of the group consisting of hydrogen, aryl, $C_{1-6}$alkyl $C_{2-6}$alkenyl, $C_{3-6}$cycloalkyl and $C_{3-6}$cycloalkenyl, and the optional substituents of $R^3$ are independently selected from one or more of the group consisting of halo, $NO_2$, $OR^5$, $NR^5_2$ and $R^5$, in which $R^5$ is independently selected from the group consisting of $C_{1-6}$alkyl, $C_{2-6}$alkenyl and $C_{2-6}$alkynyl. In embodiments of the invention, the optional substituents for $R^1$ and $R^2$ in the compounds of Formula I, are independently selected from one or more of the group consisting of halo, $NO_2$, $OR^4$, $NR^4_2$ and $R^4$, in which $R^4$ is independently selected from one or more of the group consisting of hydrogen, aryl and $C_{1-4}$alkyl and the optional substituents of $R^3$ are independently selected from one or more of the group consisting of halo, $NO_2$, $OR^5$, $NR^5_2$ and $R^5$, in which $R^5$ is independently selected from the group consisting of $C_{1-4}$alkyl. In further embodiments of the invention, the optional substituents for $R^1$ and $R^2$ in the compounds of Formula I, are independently selected from one or more of the group consisting of halo, $NO_2$, OH, $OCH_3$, $NH_2$, $N(CH_3)_2$, $CH_3$ and phenyl, and the optional substituents of $R^3$ are independently selected from one or more of the group consisting of halo, $NO_2$, OH, $OCH_3$, $NH_2$, $N(CH_3)_2$ and $CH_3$.

The compounds of Formula I also include those in which one or more of the carbon atoms in the alkyl, alkenyl and/or alkynyl groups of $R^1$, $R^2$ and/or $R^3$ is optionally replaced with a heteroatom selected from the group consisting of O, S, N, P and Si, which, where possible, is optionally substituted with one or more $C_{1-6}$alkyl groups. In an embodiment of the invention, one to three, suitably one or two, more suitably one, of the carbon atoms in the alkyl alkenyl and/or alkynyl groups of $R^1$, $R^2$ and/or $R^3$ is optionally replaced with a heteroatom selected from the group consisting of O, S, N, NH and N—$CH_3$.

In the compounds of Formula III, $R^4$ and $R^5$ represent simultaneously or independently any substituent, including but not limited to hydrogen, aryl, heteroaryl $C_{1-10}$alkyl, $C_{2-10}$alkenyl, $C_{2-10}$alkynyl, $C_{3-10}$cycloalkyl, $C_{3-10}$cycloalkenyl or $C_{3-10}$heterocyclo, which latter eight groups are optionally substituted. In embodiments of the invention, $R^4$ and $R^5$ represent simultaneously or independently hydrogen, aryl, $C_{1-6}$alkyl, $C_{2-6}$alkenyl, $C_{2-6}$alkynyl, $C_{3-6}$cycloalkyl or $C_{3-6}$cycloalkenyl, which latter six groups are optionally substituted. In further embodiments of the invention, $R^4$ and $R^5$ represent simultaneously or independently hydrogen, aryl or $C_{1-6}$alkyl, which latter two groups are optionally substituted. In still further embodiments of the invention $R^4$ and $R^5$ represent simultaneously or independently hydrogen, phenyl, and $C_{1-6}$alkyl, which latter two groups are optionally substituted. In still further embodiments of the invention $R^4$ and $R^5$ represent simultaneously or independently hydrogen, unsubstituted phenyl or methyl.

Further, in compounds of Formula III, $R^4$ and $R^5$ may be linked together to form an optionally substituted ring. In embodiments of the invention $R^4$ and $R^5$ (including the atoms to which they are attached) are linked to form an optionally substituted, suitably unsubstituted, 5- or 6-membered ring, with the linking group being a $C_3$ to $C_4$ alkylene group.

The present invention also involves the use of compounds of Formula III in which $R^6$ is selected from the group consisting of H, aryl, $C_{1-10}$alkyl, $C_{2-10}$alkenyl, $C_{2-10}$alkynyl, $C_{3-10}$cycloalkyl and $C_{3-10}$cycloalkenyl, which latter six groups are optionally substituted. In embodiments of the invention, $R^6$ is selected from the group consisting of H, aryl, $C_{1-6}$alkyl, $C_{2-6}$alkenyl, $C_{2-6}$alkynyl, $C_{3-6}$cycloalkyl and $C_{3-6}$cycloalkenyl, which latter six groups are optionally substituted. In still further embodiments of the invention, $R^6$ is selected from the group consisting of H and $C_{1-4}$alkyl, suitably H.

As stated above, the optional substituents for $R^4$, $R^5$ and $R^6$ in the compounds of Formula III, are independently selected from one or more of the group consisting of halo, $NO_2$, $OR^7$, $NR^7_2$ and $R^7$, in which $R^7$ is independently selected from the group consisting of $C_{1-6}$alkyl, $C_{2-6}$alkenyl and $C_{2-6}$alkynyl. In embodiments of the invention, the optional substituents for $R^4$, $R^5$ and $R^6$ in the compounds of Formula III, are independently selected from one or more of the group consisting of halo, $NO_2$, $OR^7$, $NR^7_2$ and $R^7$, in which $R^7$ is independently selected from one or more of the group consisting of $C_{1-4}$alkyl. In further embodiments of the invention, the optional substituents for $R^4$, $R^5$ and $R^6$ in the compounds of Formula III, are independently selected from one or more of the group consisting of halo, $NO_2$, OH, $OCH_3$, $NH_2$, $N(CH_3)_2$ and $CH_3$, The compounds of Formula III also include those in which one or more of the carbon atoms in the alkyl, alkenyl and/or alkynyl groups of $R^4$, $R^5$ and/or $R^6$ is optionally replaced with a heteroatom selected from the group consisting of O, S, N, P and Si, which, where possible, is optionally substituted with one or more $C_{1-6}$alkyl groups. In an embodiment of the invention, one to three, suitably one or two, more suitably one, of the carbon atoms in the alkyl alkenyl and/or alkynyl groups of $R^4$, $R^5$ and/or $R^6$ is optionally replaced with a heteroatom selected from the group consisting of O, S, N, NH and N—$CH_3$.

As to any of the above groups in the compounds of Formulae I-IV, that contain one or more substituents, it is understood, of course, that such groups do not contain any substitution or substitution patterns which are sterically impractical and/or synthetically non-feasible.

The present invention also relates to a very effective process for the preparation of primary amines of Formula V, wherein $R^4$ and $R^5$ are as defined in Formula IV, by selectively removing the propargyl group from the secondary amine of the Formula IV.

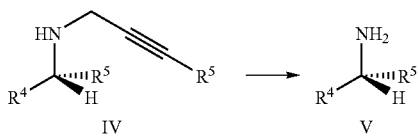

The propargyl group can be removed using any suitable method, for example using TiCl$_3$ and lithium according to the procedure of Banerji et al. (*Tetrahedron Lett.* 1999, 40, 767-770).

The process of the invention involves the catalytic hydrogenation or asymmetric hydrogenation of an imine of the Formula I or III, in the presence of a base and an achiral or chiral ruthenium complex containing a diamine ligand of the general Formula RuXY(PR$_3$)$_2$(NH$_2$—Z—NH$_2$) (VI) or RuXY(R$_2$P-Q-PR$_2$)(NH$_2$—Z—NH$_2$) (VII), where Z and Q represent a chiral or achiral linker; the ancillary ligands PR$_3$ and R$_2$P-Q-PR$_2$ represent monodentate and bidentate phosphines, respectively; and the ligands X and Y represent an anionic ligand. More particularly, the ligands X and Y are selected from the group consisting of Cl, Br, I, H, hydroxy, alkoxy and acyloxy.

In embodiments of the invention, the ligand PR$_3$:

PR$_3$ represents a chiral or achiral monodentate phosphine ligand in which R is simultaneously or independently selected from the group consisting of optionally substituted linear and branched allyl containing 1 to 8 carbon atoms, optionally substituted linear and branched alkenyl containing 2 to 8 carbon atoms, optionally substituted cycloalkyl, optionally substituted aryl, OR and NR$_2$; or two R groups bonded to the same P atom are bonded together to form a ring having 5 to 8 atoms and including the phosphorous atom to which said R groups are bonded.

In embodiments of the present invention, the ligand R$_2$P-Q-PR$_2$:

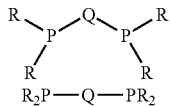

R$_2$P—Q—PR$_2$ represents a bidentate ligand in which R is simultaneously or independently selected from the group consisting of optionally substituted linear and branched alkyl containing 1 to 8 carbon atoms, optionally substituted linear and branched alkenyl containing 2 to 8 carbon atoms, optionally substituted cycloalkyl, optionally substituted aryl, OR and NR$_2$; or two R groups bonded to the same P atom are bonded together to form a ring having 5 to 8 atoms and including the phosphorous atom to which said R groups are bonded; and Q is selected from the group consisting of linear and cyclic C$_2$-C$_7$ alkylene, optionally substituted metallocenediyl and optionally substituted C$_6$-C$_{22}$ arylene.

In further embodiments of the invention, the ligand R$_2$P-Q-PR$_2$ is chiral and includes atropisomeric bis-tertiary phosphines, in which the two phosphorus atoms are linked by a biaryl backbone. More particularly, the ligand R$_2$P-Q-PR$_2$ is selected from the group consisting of BINAP, BIPHEP and BIPHEMP:

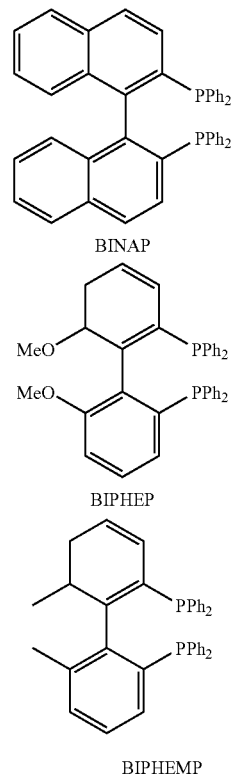

In embodiments of the invention, the bidentate phosphine is a chiral or achiral ligand of the type R$_2$P—NR$^5$—Z—NR$^5$—PR$_2$:

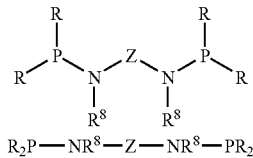

R$_2$P—NR$^8$—Z—NR$^8$—PR$_2$ wherein each R, taken separately, is independently selected from the group consisting of optionally substituted linear and branched alkyl group containing 1 to 8 carbon atoms, optionally substituted linear and branched alkenyl group containing 2 to 8 carbon atoms, optionally substituted cycloalkyl, optionally substituted aryl, OR and NR$_2$; or two R groups bonded to the same P atom are bonded together to form a ring having 5 to 8 atoms and including the phosphorous atom to which said R groups are bonded; each R$^8$, is independently selected from the group consisting of hydrogen, optionally substituted linear and branched alkyl group containing 1 to 8 carbon atoms, optionally substituted linear and branched alkenyl group containing 2 to 8 carbon atoms, optionally substituted cycloalkyl, optionally substituted aryl, OR and NR$_2$; and Z is optionally substituted linear and cyclic C$_2$-C$_7$ alkylene, optionally substituted metallocenediyl and optionally substituted $C_6$-$C_{22}$ arylene. More particularly, the ligand $R_2P$—$NR^5$—$Z$—$NR^5$—$PR_2$ (V) is selected from the group consisting of DPPACH and DCYPPACH:

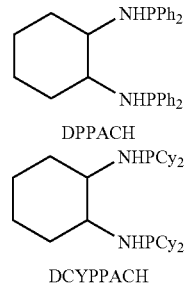

DPPACH

DCYPPACH

The present invention also includes within its scope the process in which the diamine ligand has the Formula $NH_2$—$Z$—$NH_2$:

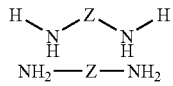

wherein Z is selected from the group consisting of optionally substituted linear and cyclic $C_2$-$C_7$ alkylene, optionally substituted metallocenediyl and optionally substituted $C_6$-$C_{22}$ arylene. In further embodiments of the invention, the diamine ligand is chiral and includes (1) compounds in which at least one of the amine-bearing centers is stereogenic, (2) compounds in which both of the amine-bearing centers are stereogenic and (3) atropisomeric bis-tertiary diamines, in which the two nitrogen atoms are linked by a biaryl backbone. Still further, the diamine ligand $NH_2$—$Z$—$NH_2$ is selected from the group consisting of CYDN and DPEN:

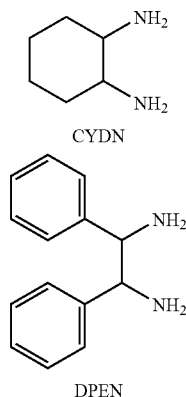

CYDN

DPEN

In embodiments of the invention, the diamine is a bidentate ligand of the Formula D-Z—$NHR^9$ in which Z is selected from the group consisting of optionally substituted linear and cyclic $C_2$-$C_7$ alkylene, optionally substituted metallocenediyl and optionally substituted $C_6$-$C_{22}$ arylene; D is an amido group donor or a chalcogenide radical selected from the group consisting of O, S, Se and Te; $NHR^9$ is an amino group donor in which $R^9$ is selected from the group consisting of hydrogen, optionally substituted linear and branched alkyl group containing 1 to 8 carbon atoms, optionally substituted linear and branched alkenyl group containing 2 to 8 carbon atoms, optionally substituted cycloalkyl and optionally substituted aryl. In more particular embodiments of the invention, D is $NR^{10}$, in which $R^{10}$ is selected from the group consisting of $S(O)_2R^{11}$, $P(O)(R^{11})_2$, $C(O)R^{11}$, $C(O)N(R^{11})_2$ and $C(S)N(R^{11})_2$, in which $R^{11}$ is independently selected from the group consisting of hydrogen, optionally substituted linear and branched alkyl group containing 1 to 8 carbon atoms, optionally substituted linear and branched alkenyl group containing 2 to 8 carbon atoms, optionally substituted cycloalkyl and optionally substituted aryl. In embodiments of the invention, the diamine is chiral and includes (1) compounds in which the amine-bearing center is stereogenic, (2) compounds in which both the donor-bearing (D) and amine-bearing centers are stereogenic. More particularly, the diamine is $CH_3C_6H_4SO_3NCHPhCHPhNH_2$.

The term "metallocenediyl" as used herein refers to a bivalent metallocene group, typically having one of the following structures:

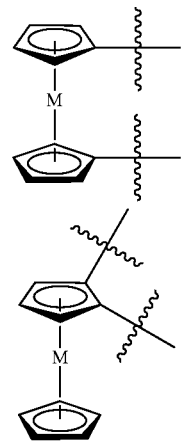

in which M is a metal, for example iron (Fe).

The term "arylene" as used herein includes biaryldiyl groups and refers to a bivalent group comprising one to three, suitably one to two, aryl groups linked together. Examples of arylene groups include, but are not limited to biphenyldiyl and binaphthyldiyl.

The term "optionally substituted" as used herein in the various ligands for the ruthenium complexes means that the corresponding group is either unsubstituted or substituted. When a group is substituted the substituents may include one to five, suitably one to three, more suitably one to two, groups selected from but not limited to alkyl, alkoxy, polyalkyleneglycol, carboxylic esters, OH, halo, cycloalkyl, aryl, and halo-substituted-aryl. As to any of the above groups that contain one or more substituents, it is understood, of course, that such groups do not contain any substitution or substitution patterns which are sterically impractical and/or synthetically non-feasible.

The term "halo" as used herein means halogen and includes chloro, fluoro, bromo and iodo.

The term "alkoxy" as used herein means saturated, cyclic, linear or branched O-alkyl groups containing from one to ten, suitably one to eight, more suitably one to six carbon atoms and includes methoxy, ethoxy, propoxy, t-butoxy and the like.

The term "acyloxy" as used herein means saturated, cyclic, linear or branched O-acyl groups containing from one to ten, suitably one to eight, more suitably one to six carbon atoms and includes acetoxy and the like.

The ruthenium catalyst complexes may be prepared, for example, as described by Abdur-Rashid et al. (*Organometallics,* 2001, 21, 1047). Many of the ligands described above are known in the art and, unless specified otherwise in the Examples, are obtained according to methods known in the art. The ligands that are new can be obtained by modifying known procedures according to the knowledge of a person skilled in the art.

As previously mentioned, the catalytic system characterizing the process of the present invention comprises a base. Said base can be the substrate itself, if the latter is basic, or any conventional base. One can cite, as non-limiting examples, organic non-coordinating bases such as DBU, tertiary organic amines, phosphazene bases, an alkaline or alkaline-earth metal carbonate, a carboxylate salt such as sodium or potassium acetate, or an alcoholate or hydroxide salt. Suitable bases are the alcoholate or hydroxide salts selected from the group consisting of the compounds of Formula $(R^{12}O)_2M'$ and $R^{12}OM''$, wherein M' is an alkaline-earth metal, M" is an alkaline metal and $R^{12}$ stands for hydrogen or a $C_1$ to $C_6$ linear or branched alkyl radical. Also within the scope of the present invention, the base may be an organic non-coordinating base.

A typical process implies the mixture of the substrate with the ruthenium complex and a base, possibly in the presence of a solvent, and then treating such a mixture with molecular hydrogen at a chosen pressure and temperature.

The complexes can be added to the reaction medium in a large range of concentrations. As non-limiting examples, one can cite substrate to complex (S/com) ratio of 20 to $10^5$. Preferably, the substrate to complex ratio will be in the range of 1000 to $10^4$, respectively. It goes without saying that the optimum concentration of complex will depend on the nature of the latter and on the pressure of $H_2$ used during the process.

Useful quantities of base, added to the reaction mixture, may be comprised in a relatively large range. One can cite, as non-limiting examples, ranges between 1 to 50000 molar equivalents relative to the complex, preferably 10 to 2000. However, it should be noted that it is also possible to add a small amount of base (e.g. base/com=1 to 3) to achieve high hydrogenation yields.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. Still further, the solvent may be an amine solvent. A person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars). Again, a person skilled in the art is well able to adjust the pressure as a function of the catalyst load and of the dilution of the substrate in the solvent. As examples, one can cite typical pressures of 1 to $40 \times 10^5$ Pa (1 to 40 bar).

The temperature at which the hydrogenation can be carried out is comprised between 0° C. and 100° C., more preferably in the range of between 20° C. and 60° C. Of course, a person skilled in the art is also able to select the preferred temperature as a function of the melting and boiling point of the starting and final products.

The following non-limiting examples are illustrative of the present invention:

EXAMPLES

Materials and Methods

The invention will now be described in further details by way of the following examples, wherein the temperatures are indicated in degrees centigrade and the abbreviations have the usual meaning in the art. The ligand R,R-DPPACH is a known compound that was previously used in rhodium complexes for the hydrogenation of C═C double bonds (Fioriani et al., *J. Mol. Catal.,* 1979, 5, 303), (Onuma et al., *Bull. Chem. Soc. Jpn.,* 1980, 53, 2012; *Chem. Lett.,* 1980, 5, 481).

All the procedures described hereafter have been carried out under an inert atmosphere unless stated otherwise. Hydrogenations were carried out in open glass tubes placed inside a stainless steel autoclave or Schlenk flasks attached to a vacuum line. Hydrogen gas was used as received. All preparations and manipulations were carried out under $H_2$, $N_2$ or Ar atmospheres with the use of standard Schlenk, vacuum line and glove box techniques in dry, oxygen-free solvents. Tetrahydrofuran (THF), diethyl ether ($Et_2O$) and hexanes were dried and distilled from sodium benzophenone ketyl. Deuterated solvents were degassed and dried over activated molecular sieves. Ruthenium trichloride, triphenylphosphine, RR-DPEN, R,R-CYDN, ketones and amines were purchased from Aldrich. Imines were prepared using previously reported procedures (*Organometallics* 2001, 21, 1047; *J. Am. Chem. Soc* 1996, 118, 6784; *J. Am. Chem. Soc* 1994, 116, 8952; *J. Org. Chem. Soc* 1993, 58, 7627). Selective removal of the N-propargyl protecting group from amines followed the procedure which was previously reported by Banerji et al. (*Tetrahedron Lett.* 1999, 40, 767). The precursor complex $RuHCl(PPh_3)_3$ was prepared by a modification of the procedure reported by Schunn et al. (*Inorg. Synth.* 1970, 131). The complexes $RuHCl(R-BINAP)(PPh_3)$, $RuHCl(R,R-DPPACH)(PPh_3)$, $RuHCl(R-BINAP)(RR-CYDN)$, $RuHCl(R-BINAP)$ $(R,R-DPEN)$, $RuHCl(RR-DPPACH)(R,R-CYDN)$ and $RuHCl(RR-DPPACH)$ $(R,R-DPEN)$ were prepared as described in *Organometallics,* 2001, 21, 1047. NMR spectra were recorded on either a Varian Gemini 300 MHz spectrometer (300 MHz for $^1H$, 75 MHz for $^{13}C$ and 121.5 for $^{31}P$) or a Varian Unity 400 MHz spectrometer (400 MHz for $^1H$ and 100 MHz for $^{13}C$). All $^{31}P$ spectra were recorded with proton decoupling and $^{31}P$ chemical shifts were measured relative to 85% $H_3PO_4$ as an external reference. $^1H$ and $^{13}C$ chemical shifts were measured relative to partially deuterated solvent peaks but are reported relative to tetramethylsilane.

Structure of the Ligands Used in the Examples are Shown Below:

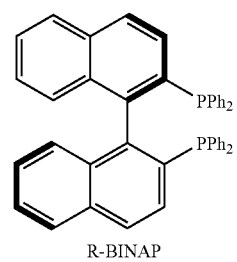

R-BINAP

-continued

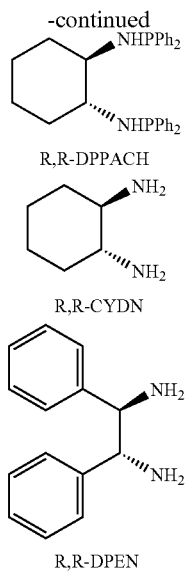

R,R-DPPACH

R,R-CYDN

R,R-DPEN

Example 1

General Procedure for Catalytic Hydrogenation

A solution of the required imine dissolved in benzene was added to a mixture of the catalyst (0.1-0.5%) and KO$^t$Bu (10-50 mg) in a 50 ml Parr hydrogenation reactor (fitted with a removable glass liner and a magnetic stirring bar). The reactor was then purged several times with H$_2$ gas, pressurized to the desired pressure (10-50 bar) and stirred vigorously at the required temperature. The pressure was periodically released and the hydrogenation reaction monitored by removing a sample of the reaction mixture and measuring its $^1$H NMR spectrum. If required, the mixture was re-pressurized with H$_2$ gas and the reaction continued until either the hydrogenation is complete or no further change in the composition was observed (NMR). Upon completion, hexane (10 ml) was added to the reaction mixture, which was then eluted (hexane) through a short column of silica gel in order to remove the spent catalyst and KO$^t$Bu. Evaporation of the hexane under reduced pressure yielded the product.

Results of the Catalytic hydrogenation using the series of RuHCl(diphosphine)(diamine) complexes are summarized below.

Example 1.1

Hydrogenation of N-(Benzylidene)methylamine

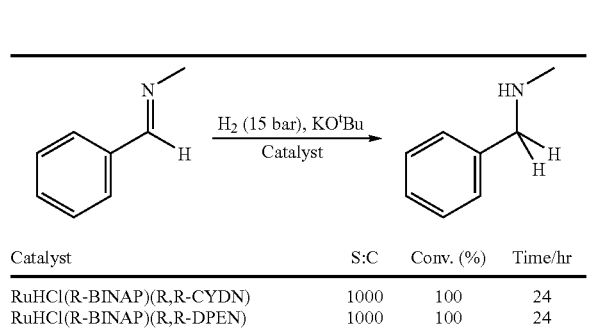

| Catalyst | S:C | Conv. (%) | Time/hr |
|---|---|---|---|
| RuHCl(R-BINAP)(R,R-CYDN) | 1000 | 100 | 24 |
| RuHCl(R-BINAP)(R,R-DPEN) | 1000 | 100 | 24 |

-continued

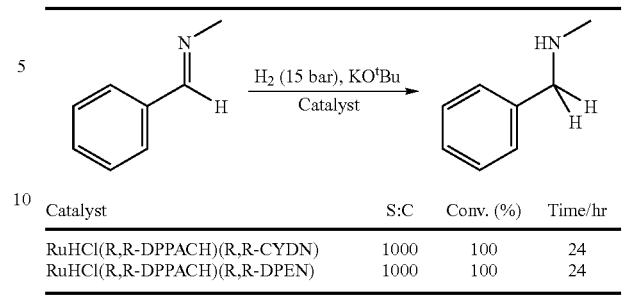

| Catalyst | S:C | Conv. (%) | Time/hr |
|---|---|---|---|
| RuHCl(R,R-DPPACH)(R,R-CYDN) | 1000 | 100 | 24 |
| RuHCl(R,R-DPPACH)(R,R-DPEN) | 1000 | 100 | 24 |

Example 1.2

Hydrogenation of N-(1-Phenylethylidene)methylamine

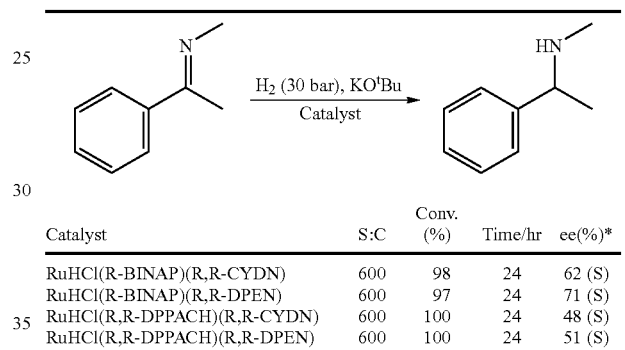

| Catalyst | S:C | Conv. (%) | Time/hr | ee(%)* |
|---|---|---|---|---|
| RuHCl(R-BINAP)(R,R-CYDN) | 600 | 98 | 24 | 62 (S) |
| RuHCl(R-BINAP)(R,R-DPEN) | 600 | 97 | 24 | 71 (S) |
| RuHCl(R,R-DPPACH)(R,R-CYDN) | 600 | 100 | 24 | 48 (S) |
| RuHCl(R,R-DPPACH)(R,R-DPEN) | 600 | 100 | 24 | 51 (S) |

*The ee was determined from the rotation ($\alpha_D$) of N-methyl-1-phenylethylamine.

Example 1.3

Hydrogenation of N-(Benzylhydrylidene)methylamine

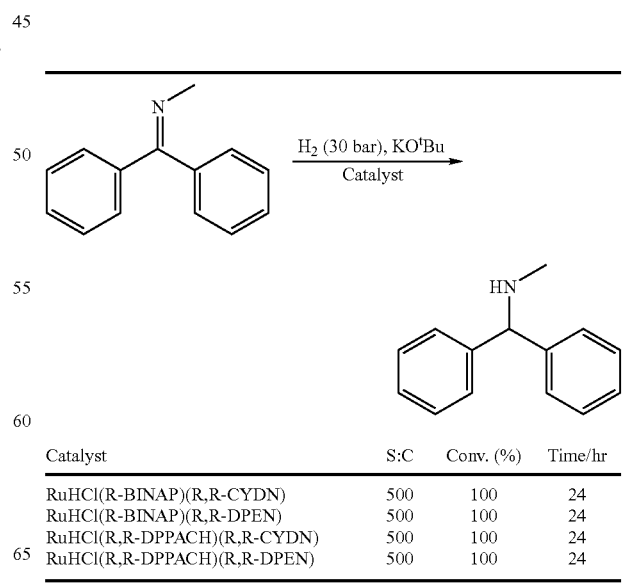

| Catalyst | S:C | Conv. (%) | Time/hr |
|---|---|---|---|
| RuHCl(R-BINAP)(R,R-CYDN) | 500 | 100 | 24 |
| RuHCl(R-BINAP)(R,R-DPEN) | 500 | 100 | 24 |
| RuHCl(R,R-DPPACH)(R,R-CYDN) | 500 | 100 | 24 |
| RuHCl(R,R-DPPACH)(R,R-DPEN) | 500 | 100 | 24 |

Example 1.4

Hydrogenation of N-(Benzylidene)ethylamine

| Catalyst | S:C | Conv. (%) | Time/hr |
|---|---|---|---|
| RuHCl(R-BINAP)(R,R-CYDN) | 1000 | 100 | 24 |
| RuHCl(R-BINAP)(R,R-DPEN) | 1000 | 100 | 24 |
| RuHCl(R,R-DPPACH)(R,R-CYDN) | 1000 | 100 | 24 |
| RuHCl(R,R-DPPACH)(R,R-DPEN) | 1000 | 100 | 24 |

Example 1.5

Hydrogenation of N-(1-Phenylethylidene)ethylamine

| Catalyst | S:C | Conv. (%) | Time/hr |
|---|---|---|---|
| RuHCl(R-BINAP)(R,R-CYDN) | 500 | 95 | 36 |
| RuHCl(R-BINAP)(R,R-DPEN) | 500 | 98 | 36 |
| RuHCl(R,R-DPPACH)(R,R-CYDN) | 500 | 100 | 24 |
| RuHCl(R,R-DPPACH)(R,R-DPEN) | 500 | 100 | 24 |

Example 1.6

Hydrogenation of N-(1-Phenylethylidene)-2-propylamine

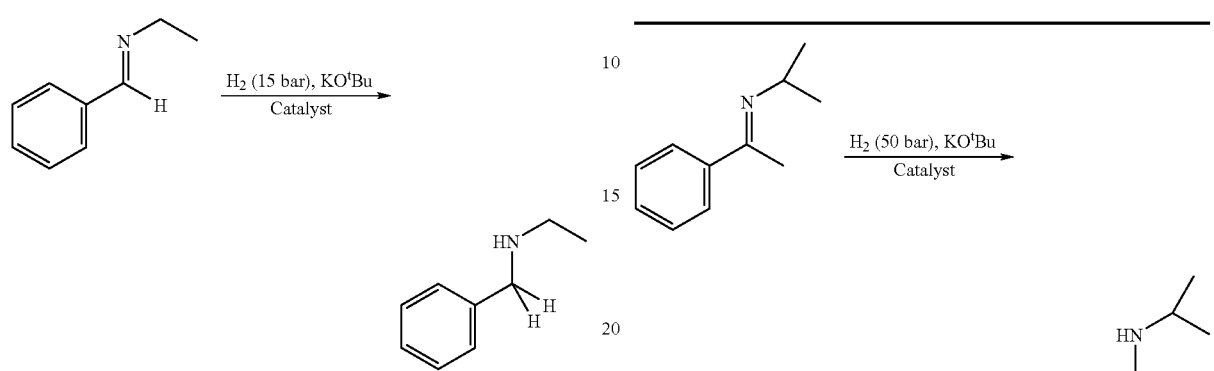

| Catalyst | S:C | Conv. (%) | Time/hr |
|---|---|---|---|
| RuHCl(R-BINAP)(R,R-CYDN) | 500 | 75 | 36 |
| RuHCl(R-BINAP)(R,R-DPEN) | 500 | 72 | 36 |
| RuHCl(R,R-DPPACH)(R,R-CYDN) | 500 | 87 | 24 |
| RuHCl(R,R-DPPACH)(R,R-DPEN) | 500 | 91 | 24 |

Example 1.7

Hydrogenation of N-(1-Phenylethylidene)cyclopentylamine

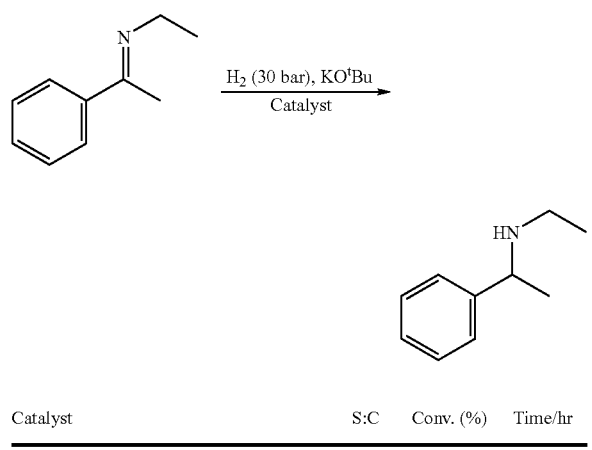

| Catalyst | S:C | Conv. (%) | Time/hr |
|---|---|---|---|
| RuHCl(R-BINAP)(R,R-CYDN) | 200 | 91 | 36 |
| RuHCl(R-BINAP)(R,R-DPEN) | 200 | 83 | 36 |
| RuHCl(R,R-DPPACH)(R,R-CYDN) | 200 | 97 | 36 |
| RuHCl(R,R-DPPACH)(R,R-DPEN) | 200 | 95 | 36 |

Example 1.8

Hydrogenation of 2-phenyl-1-pyrroline

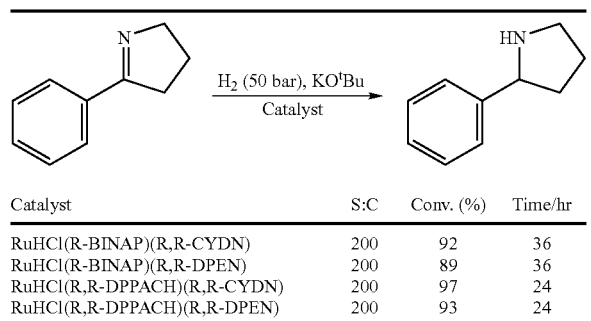

| Catalyst | S:C | Conv. (%) | Time/hr |
|---|---|---|---|
| RuHCl(R-BINAP)(R,R-CYDN) | 200 | 92 | 36 |
| RuHCl(R-BINAP)(R,R-DPEN) | 200 | 89 | 36 |
| RuHCl(R,R-DPPACH)(R,R-CYDN) | 200 | 97 | 24 |
| RuHCl(R,R-DPPACH)(R,R-DPEN) | 200 | 93 | 24 |

Example 1.9

Hydrogenation of 2-phenyl-3,4,5,6-tetrahydropyridine

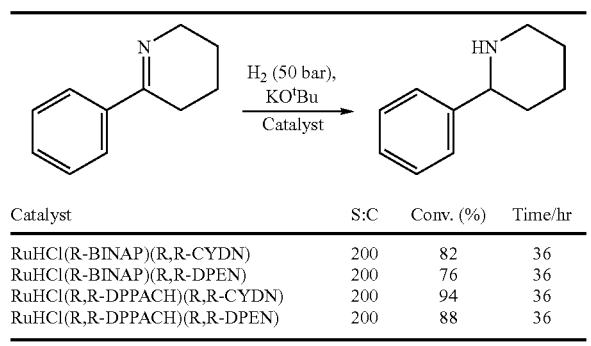

| Catalyst | S:C | Conv. (%) | Time/hr |
|---|---|---|---|
| RuHCl(R-BINAP)(R,R-CYDN) | 200 | 82 | 36 |
| RuHCl(R-BINAP)(R,R-DPEN) | 200 | 76 | 36 |
| RuHCl(R,R-DPPACH)(R,R-CYDN) | 200 | 94 | 36 |
| RuHCl(R,R-DPPACH)(R,R-DPEN) | 200 | 88 | 36 |

Example 1.10

Hydrogenation of N-(Benzylidene)propargylamine

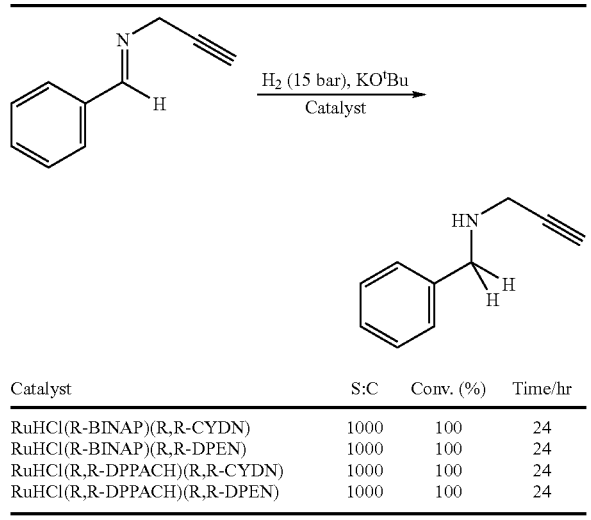

| Catalyst | S:C | Conv. (%) | Time/hr |
|---|---|---|---|
| RuHCl(R-BINAP)(R,R-CYDN) | 1000 | 100 | 24 |
| RuHCl(R-BINAP)(R,R-DPEN) | 1000 | 100 | 24 |
| RuHCl(R,R-DPPACH)(R,R-CYDN) | 1000 | 100 | 24 |
| RuHCl(R,R-DPPACH)(R,R-DPEN) | 1000 | 100 | 24 |

Example 1.11

Hydrogenation of N-(1-Phenylethylidene)propargylamine

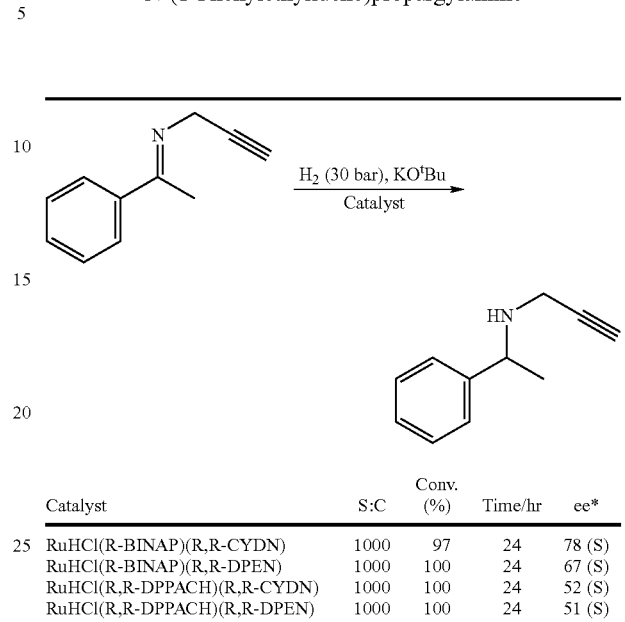

| Catalyst | S:C | Conv. (%) | Time/hr | ee* |
|---|---|---|---|---|
| RuHCl(R-BINAP)(R,R-CYDN) | 1000 | 97 | 24 | 78 (S) |
| RuHCl(R-BINAP)(R,R-DPEN) | 1000 | 100 | 24 | 67 (S) |
| RuHCl(R,R-DPPACH)(R,R-CYDN) | 1000 | 100 | 24 | 52 (S) |
| RuHCl(R,R-DPPACH)(R,R-DPEN) | 1000 | 100 | 24 | 51 (S) |

*The ee was determined from the rotation ($\alpha_D$) of the de-protected 1-phenylethylamine.

Example 2

Removal of the Protecting Group

Example 2.1

Removal of the protecting group from N-(Benzyl)propargylamine in Example 1.10

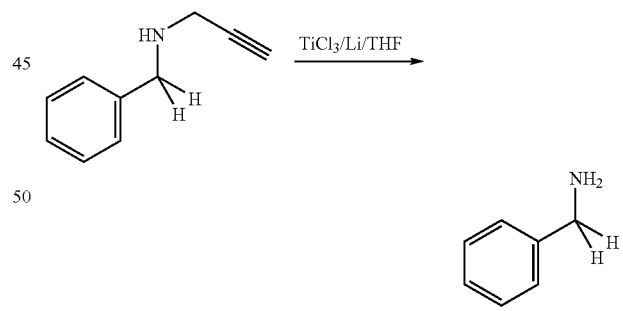

The procedure reported by Banerji et al. (*Tetrahedron Lett.* 1999, 40, 767-770) was used to selectively remove the N-propargyl protecting group. A mixture of $TiCl_3$ (1.54 g, 10 mmol) and lithium (231 mg, 33 mmol) was refluxed for 3 hours under argon in THF (40 ml). A solution of N-(Benzyl)propargylamine (500 mg, 3.4 mmol) in THF (5 ml) was added to the LVT reagent and stirred for 1 hour at room temperature. The reaction mixture was diluted with hexane-ethyl acetate mixture (70:30) and filtered through celite. The filtrate washed with brine, dried ($Na_2SO_4$), and concentrated under vacuum.

The crude product was purified using chromatography (SiO$_2$) to yield benzylamine (245 mg, 66%).

Example 2.2

Removal of protecting group from N-(1-Phenylethyl)propargylamine in Example 1.11

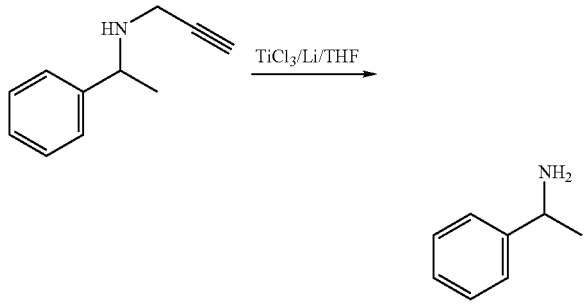

A solution of N-(1-Phenylethyl)propargylamine (500 mg, 3.1 mmol) in THF (5 ml) was added to the LVT reagent prepared as described in Example 2.1 above, and the resulting mixture stirred for 2 hours at room temperature. The reaction mixture was diluted with hexane-ethyl acetate mixture (70:30) and filtered through celite. The filtrate washed with brine, dried (Na$_2$SO$_4$), and concentrated under vacuum. The crude product was purified using chromatography (SiO$_2$) to yield 1-phenylethylamine (290 mg, 77%). The rotation ($\alpha_D$) of the deprotected 1-phenylethylamine was used to determine the ee of the products in Example 1.11.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

What is claimed is:

1. A process for the hydrogenation and/or asymmetric hydrogenation of an imine of Formula (I) to an amine of Formula (II) and/or its other enantiomer:

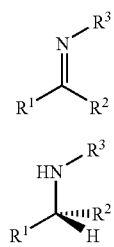

wherein
$R^1$ is selected from the group consisting of aryl and heteroaryl, which two groups are optionally substituted;
$R^2$ is selected from the group consisting of aryl, heteroaryl, $C_{1-10}$alkyl, $C_{2-10}$alkenyl, $C_{2-10}$alkynyl, $C_{3-10}$cycloalkyl, $C_{3-10}$cycloalkenyl and $C_{3-10}$heterocyclo, which latter eight groups are optionally substituted; and
$R^3$ is selected from the group consisting of optionally substituted $C_1$ to $C_2$ alkyl and optionally substituted $C_{3-10}$cycloalkyl;
wherein the optional substituents of $R^1$ and $R^2$ are independently selected from one or more of the group consisting of halo, NO$_2$, OR$^4$, NR$^4_2$ and R$^4$, in which R$^4$ is independently selected from one or more of the group consisting of hydrogen, aryl, $C_{1-6}$alkyl, $C_{2-6}$alkenyl, $C_{3-6}$cycloalkyl and $C_{3-6}$cycloalkenyl;
the optional substituents of $R^3$ are independently selected from one or more of the group consisting of halo, NO$_2$, OC$_{1-6}$alkyl, N(C$_{1-6}$alkyl)$_2$ and C$_{1-6}$alkyl; and
one or more of the carbon atoms in the alkyl, alkenyl and/or alkynyl groups of $R^1$, $R^2$ and/or $R^3$ is optionally replaced with a heteroatom selected from the group consisting of O, S, N, O and Si, which, where possible, is optionally substituted with one or more C$_{1-6}$alkyl groups;
said process comprising the steps of reacting imines of Formula (I) in the presence of a H$_2$ pressure between 30 bar and 80 bar, a base and a catalytic system in which the catalytic system comprises a ruthenium complex comprising (I) a diamine and (2) a diphosphine ligand or monodentate phosphine ligand.

2. The process according to claim 1, wherein the amine of Formula (II) or its opposite enantiomer, is produced in enantiomerically enriched form.

3. The process according to claim 1, wherein $R^1$ is optionally substituted aryl.

4. The process according to claim 3, wherein $R^1$ is optionally substituted phenyl.

5. The process according to claim 4, wherein $R^1$ is unsubstituted phenyl.

6. The process according to claim 3, wherein $R^2$ is selected from the group consisting of aryl, $C_{1-6}$alkyl, $C_{2-6}$alkenyl, $C_{2-6}$alkynyl, $C_{3-6}$cycloalkyl and $C_{3-6}$cycloalkenyl, which latter six groups are optionally substituted.

7. The process according to claim 6, wherein $R^2$ is selected from the group consisting of aryl and $C_{1-6}$alkyl, which latter two groups are optionally substituted.

8. The process according to claim 7, wherein $R^2$ is selected from the group consisting of phenyl, and $C_{1-6}$alkyl, which latter two groups are optionally substituted.

9. The process according to claim 8, wherein $R^2$ is selected from the group consisting of unsubstituted phenyl and methyl.

10. The process according to claim 3, wherein $R^3$ is selected from the group consisting of optionally substituted $C_1$ to $C_2$ alkyl and optionally substituted $C_{3-6}$cycloalkyl.

11. The process according to claim 10, wherein $R^3$ is methyl, ethyl, i-propyl, cyclopropyl, cyclobutyl, cyclopentyl or cyclohexyl, which latter four groups are unsubstituted.

12. The process according to claim 3, wherein the optional substituents for $R^1$ and $R^2$ in the compounds of Formula I, are independently selected from one or more of the group consisting of halo, NO$_2$, OR$^4$, NR$^4_2$ and R$^4$, in which R$^4$ is independently selected from one or more of the group consisting of hydrogen, aryl and C$_{1-4}$alkyl, and the optional substituents of R$^3$ are independently selected from one or more of the group consisting of halo, NO$_2$, OC$_{1-4}$alkyl, N(C$_{1-4}$alkyl)$_2$ and C$_{1-4}$alkyl.

13. The process according to claim 12, wherein the optional substituents for $R^1$ and $R^2$ in the compounds of Formula I, are independently selected from one or more of the group consisting of halo, $NO_2$, OH, $OCH_3$, $NH_2$, $N(CH_3)_2$, $CH_3$ and phenyl and the optional substituents of $R^3$ are independently selected from one or more of the group consisting of halo, $NO_2$, OH, $OCH_3$, $NH_2$, $N(CH_3)_2$ and $CH_3$.

14. The process according to claim 3, wherein one to three of the carbon atoms in the alkyl, alkenyl and/or alkynyl groups of $R^1$, $R^2$ and/or $R^3$ is optionally replaced with a heteroatom selected from the group consisting of O, S, N, NH and N—$CH_3$.

15. The process according to claim 14, wherein suitably one of the carbon atoms in the alkyl, alkenyl and/or alkynyl groups of $R^1$, $R^2$ and/or $R^3$ is optionally replaced with a heteroatom selected from the group consisting of O, S, N, NH and N—$CH_3$.

16. The process according to claim 1, wherein said ruthenium complex has the general Formula $RuXY(PR_3)_2(NH_2-Z-NH_2)$ (III) or $RuXY(R_2P-Q-PR_2)(NH_2-Z-NH_2)$ (IV), where Z and Q represent a chiral or achiral linker; the ancilliary ligands $PR_3$ and $R_2P-Q-PR_2$ represent monodentate and bidentate phosphines, respectively; and the ligands X and Y represent an anionic ligand.

17. The process according to claim 16, wherein the ligand $PR_3$:

PR₃ represents a chiral or achiral monodentate phosphine ligand in which R is simultaneously or independently selected from the group consisting of optionally substituted linear and branched alkyl containing 1 to 8 carbon atoms, optionally substituted linear and branched alkenyl containing 2 to 8 carbon atoms, optionally substituted cycloalkyl, optionally substituted aryl, OR and $NR_2$; or two R groups bonded to the same P atom are bonded together to form a ring having 5 to 8 atoms and including the phosphorous atom to which said R groups are bonded.

18. The process according to claim 16, wherein the ligand $R_2P-Q-PR_2$:

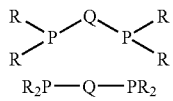

$R_2P-Q-PR_2$ represents a bidentate ligand in which R is simultaneously or independently selected from the group consisting of optionally substituted linear and branched alkyl containing 1 to 8 carbon atoms, optionally substituted linear and branched alkenyl containing 2 to 8 carbon atoms, optionally substituted cycloalkyl, optionally substituted aryl, OR and $NR_2$; or two R groups bonded to the same P atom are bonded together to form a ring having 5 to 8 atoms and including the phosphorous atom to which said R groups are bonded; and Q is selected from the group consisting of linear and cyclic $C_2$-$C_7$ alkylene, optionally substituted metallocenediyl and optionally substituted $C_6$-$C_{22}$ arylene.

19. The process according to claim 18, wherein the ligand $R_2P-Q-PR_2$ is chiral and includes atropisomeric bis-tertiary phosphines, in which the two phosphorus atoms are linked by a biaryl backbone.

20. The process according to claim 19, wherein the ligand $R_2P-Q-PR_2$ is selected from the group consisting of BINAP, BIPHEP and BIPHEMP.

21. The process according to claim 16, wherein the bidentate phosphine is a chiral or achiral ligand of the type $R_2P-NR^8-Z-NR^8-PR_2$:

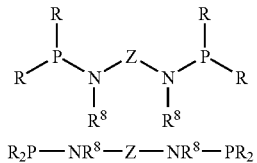

$R_2P-NR^8-Z-NR^8-PR_2$ wherein each R, taken separately, is independently selected from the group consisting of optionally substituted linear and branched alkyl containing 1 to 8 carbon atoms, optionally substituted linear and branched alkenyl containing 2 to 8 carbon atoms, optionally substituted cycloalkyl, optionally substituted aryl, OR and $NR_2$; or two R groups bonded to the same P atom are bonded together to form a ring having 5 to 8 atoms and including the phosphorous atom to which said R groups are bonded; each $R^8$, taken separately, is independently selected from the group consisting of hydrogen, optionally substituted linear and branched alkyl and alkenyl containing 1 to 8 carbon atoms, optionally substituted cycloalkyl, optionally substituted aryl, OR and $NR_2$; and Z is optionally substituted linear and cyclic $C_2$-$C_7$ alkylene, optionally substituted metallocenediyl and optionally substituted $C_6$-$C_{22}$ arylene.

22. The process according to claim 21, wherein the ligand $R_2P-NR^8-Z-NR^8-PR_2$ is selected from the group consisting of DPPACH and DCYPPACH.

23. The process according to claim 1, wherein the diamine ligand has the Formula $NH_2-Z-NH_2$:

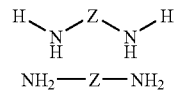

$NH_2-Z-NH_2$ wherein Z is selected from the group consisting of optionally substituted linear and cyclic $C_2$-$C_7$ alkylene, optionally substituted metallocenediyl and optionally substituted $C_6$-$C_{22}$ arylene.

24. The process according to claim 23, wherein the diamine ligand is chiral and includes (1) compounds in which at least one of the amine-bearing centers is stereogenic, (2) compounds in which both of the amine-bearing centers are stereogenic and (3) atropisomeric bis-tertiary diamines, in which the two nitrogen atoms are linked by a biaryl backbone.

25. The process according to claim 23, wherein the diamine ligand $NH_2-Z-NH_2$ is selected from the group consisting of CYDN and DPEN.

26. The process according to claim 1, wherein the diamine is a bidentate ligand of the Formula D-Z—$NHR^9$ in which Z is selected from the group consisting of optionally substituted linear and cyclic $C_2$-$C_7$ alkylene, optionally substituted metallocenediyl and optionally substituted $C_6$-$C_{22}$ arylene; D is an amido group donor or a chalcogenide radical selected from the group consisting of O, S, Se and Te; NHR$^9$ is an amino group donor in which R$^9$ is selected from the group consisting of hydrogen, optionally substituted linear and branched alkyl and alkenyl containing 1 to 8 carbon atoms, optionally substituted cycloalkyl and optionally substituted aryl.

27. The process according to claim 26, wherein D is NR$^{10}$, wherein R$^{10}$ is selected from the group consisting of S(O)$_2$R$^{10}$, P(O)(R$^{10}$)$_2$, C(O)R$^{10}$, C(O)N(R$^{10}$)$_2$ and C(S)N(R$^{10}$)$_2$, in which R$^{10}$ is independently selected from the group consisting of hydrogen, optionally substituted linear and branched alkyl and alkenyl containing 1 to 8 carbon atoms, optionally substituted cycloalkyl and optionally substituted aryl.

28. The process according to claim 26, wherein the diamine is chiral and includes (1) compounds in which the amine-bearing center is stereogenic, (2) compounds in which both the donor-bearing (D) and amine-bearing centers are stereogenic.

29. The process according to claim 28, wherein the diamine is CH$_3$C$_6$H$_4$SO$_3$NCHPhCHPhNH$_2$.

30. The process according to claim 1, wherein the ligands X and Y is selected from the group consisting of Cl, Br, I, H, hydroxy, alkoxy and acyloxy.

31. The process according to claim 1, wherein the base is an alcoholate or an hydroxide salt selected from the group consisting of compounds of the Formula (R$^{12}$O)$_2$M' and R$^{12}$OM'', in which M' is an alkaline-earth metal, M'' is an alkaline metal and R$^{12}$ is selected from the group consisting of hydrogen, C$_1$ to C$_6$ linear and branched alkyl.

32. The process according to claim 1, wherein the base is an organic non-coordinating base.

33. The process according to claim 32, wherein the base is selected from the group consisting of DBU, NR$_3$ and phosphazene.

34. The process according to claim 1, wherein the hydrogenation is carried out in the absence of a solvent.

35. The process according to claim 1, wherein the hydrogenation reaction is carried out in the presence of a solvent.

36. The process according to claim 35, wherein the solvent is selected from the group consisting of benzene, toluene, xylene, hexane, cyclohexane, tetrahydrofuran, primary and secondary alcohols, and mixtures thereof.

37. The process according to claim 35, wherein the hydrogenation is carried out in an amine solvent.

* * * * *